(12) United States Patent
Lashkari

(10) Patent No.: US 8,888,765 B1
(45) Date of Patent: Nov. 18, 2014

(54) SYSTEM AND METHOD FOR USE OF INFRARED BINOCULAR INDIRECT OPHTHALMOSCOPES IN IMAGING AND PHOTODYNAMIC THERAPY

(76) Inventor: Kameran Lashkari, Boston, MA (US)

( * ) Notice: Subject to any disclaimer, the term of this patent is extended or adjusted under 35 U.S.C. 154(b) by 987 days.

(21) Appl. No.: 12/578,306

(22) Filed: Oct. 13, 2009

Related U.S. Application Data

(60) Provisional application No. 61/104,357, filed on Oct. 10, 2008.

(51) Int. Cl.
*A61B 3/10* (2006.01)
*A61B 18/18* (2006.01)

(52) U.S. Cl.
USPC ................................ 606/4; 351/246; 351/205

(58) Field of Classification Search
CPC ........ A61B 3/103; A61B 3/1015; A61B 3/14; A61B 3/12; A61F 9/008; A61F 2009/00872; A61F 2009/00887
USPC .............................. 351/246, 205–206; 606/4–6
See application file for complete search history.

(56) References Cited

U.S. PATENT DOCUMENTS

| | | | |
|---|---|---|---|
| 4,917,486 A * | 4/1990 | Raven et al. | 351/221 |
| 5,841,509 A | 11/1998 | Harooni et al. | |
| 6,089,716 A | 7/2000 | Lashkari et al. | |
| 6,350,031 B1 | 2/2002 | Lashkari et al. | |
| 6,361,167 B1 * | 3/2002 | Su et al. | 351/206 |
| 6,574,432 B2 | 6/2003 | Nanjyo | |
| 6,578,965 B2 | 6/2003 | Grant | |
| 6,796,978 B2 | 9/2004 | Gerlach et al. | |
| 6,826,359 B1 | 11/2004 | Takeda | |
| 6,984,655 B1 * | 1/2006 | Mori et al. | 514/410 |
| 7,168,806 B2 | 1/2007 | Abe | |
| 7,281,800 B2 | 10/2007 | Vilser | |
| 7,331,670 B2 | 2/2008 | Ichikawa | |
| 7,344,248 B2 | 3/2008 | Zorn et al. | |
| 2004/0151008 A1 * | 8/2004 | Artsyukhovich et al. | 362/572 |
| 2004/0233388 A1 * | 11/2004 | Artsyukhovich et al. | 351/216 |
| 2006/0258629 A1 * | 11/2006 | Freeman | 514/150 |
| 2008/0291397 A1 * | 11/2008 | Tesar | 351/221 |

FOREIGN PATENT DOCUMENTS

| | | |
|---|---|---|
| EP | 1 138 255 A1 | 10/2001 |
| EP | 1 818 008 A1 | 8/2007 |

* cited by examiner

*Primary Examiner* — James Greece
(74) *Attorney, Agent, or Firm* — Loginov & Associates, PLLC; William A. Loginov

(57) ABSTRACT

An infrared binocular indirect ophthalmoscope (iBIO) is provided to the simultaneous examination and treatment of the human eye. The iBIO operates in infrared light, at long wavelengths to penetrate the eye and image the retina. The iBIO can further include a treatment beam to activate an appropriate agent that has been injected in the human eye, for performing a treatment on the eye. The photosensitizing agent can include any photosensitive material that is activated at a predetermined wavelength. Can be useful in photodynamic therapy and other types of treatment for simultaneous examination and treatment of the human eye.

11 Claims, 3 Drawing Sheets

US 8,888,765 B1

SYSTEM AND METHOD FOR USE OF INFRARED BINOCULAR INDIRECT OPHTHALMOSCOPES IN IMAGING AND PHOTODYNAMIC THERAPY

RELATED APPLICATIONS

This application claims the benefit of U.S. Provisional Patent Application Ser. No. 61/104,357, filed Oct. 10, 2008, entitled DESIGN AND IMPLEMENTATION OF NEW GENERATION (INFRARED) BINOCULAR INDIRECT OPHTHALMOSCOPES FOR IMAGING AND PHOTODYNAMIC THERAPY, the entire disclosure of which is herein incorporated by reference.

FIELD OF THE INVENTION

The present invention relates to ophthalmoscopes and, more particularly, to second generation binocular indirect ophthalmoscopes for observing and treating diseases of the human eye.

BACKGROUND OF THE INVENTION

Since its invention in the early 1950's by Charles L. Schepens, M.D., the binocular indirect ophthalmoscope (BIO) has become an integral part of a routine eye exam among vision care providers. Using visible light, the first generation BIO allowed direct visualization of retinal anatomy and pathology by directing light to the fundus and a hand-held condensing lens, and using the reflected light to create a virtual (indirect) image of the fundus above the plane of the eye. The BIO has been the instrument of choice for medical and surgical management of patients with retinal disease including examination and treatment of peripheral retinal pathology, retinal detachment, vitreous hemorrhage and ocular trauma.

Binocular indirect ophthalomoscopy offers several advantages of direct ophthalmoscopy, including stereopsis and a much enlarged field of view and depth of field. In general, a binocular indirect ophthalmoscope includes a light source and two light observation paths for viewing the retina. The dual observation path allows for stereopsis (i.e., 3-D vision) of a patient's eye. In one binocular indirect ophthalmoscope, such as U.S. Pat. No. 6,350,031 entitled ELECTRO-OPTIC BINOCULAR INDIRECT OPHTHALMOSCOPE, incorporated herein by reference, the light source can include a near infrared (e.g., 810 nm) source.

The original Schepens BIO uses visible light to perform the imaging of the retina, which disadvantageously requires the pupils to be dilated, thereby interfering with an individual's ability to continue normal activities subsequent to the examination procedure. Eliminating the dilatation step can be a critical issue when dealing with children, or a patient suffering from other injuries, such as in a trauma center or on a battle field. Further, the visible light spectrum transmits short wavelengths of light to generate the image of the retina. The visible light spectrum as the illumination assembly for the BIO provides a methodology in which to examine an image of the retina, through the use of at least a pair of lenses. These lenses appropriately focus and collimate the visible light to illuminate the fundus and obtain an image of the fundus.

It is desirable to provide a device that utilizes illumination to provide a superior image of the subretinal and choroidal layers by penetrating deeper into the eye with longer wavelengths. It is further desirable to provide a procedure by which a medical treatment may be performed on a human eye while a practitioner, ophthalmologist or other individual tasked with the examination acquires an image of the retina.

SUMMARY OF THE INVENTION

This invention overcomes the disadvantages of the prior art by providing an infrared Binocular Indirect Ophthalmoscope (iBIO or "infrared ophthalmoscope")) for the examination and simultaneous treatment of the human eye. This iBIO operates in infrared light, at wavelengths that are long so as to penetrate the eye and provide a superior image. It further provides a treatment beam light source to activate an appropriate agent that has been intravenously injected so as to enter the human eye, for thereby performing a treatment on the eye.

The infrared ophthalmoscope includes a light source, such as a laser or a light emitting diode (LED), which is imaged on a beam separator. A collimating lens is disposed at its focal length from the beam separator that collimates the light, and an illuminating lens forms an image of the light source in the pupil of the eye. The light returning from the retina is then collimated by the optics of the eye, and an image of the retina is formed at the focal length of the illuminating lens. The image of the retina is then passed through the collimating lens to again collimate the image. Then, at the beam separator, most of the returned light is deflected into a camera for examination and therapy implementation.

This system and method can illustratively employ reactive agent provided to the person being examined that is a photosensitive agent. The agent can be activated by a treatment light source to perform a medical treatment on the eye. Conditions that can be beneficially treated in accordance to the illustrative embodiments illustratively include (1) choroidal neovascularization secondary to age-related macular degeneration and other inflammatory or idiopathic entities; (2) peripheral retinal vascular disease including diabetic retinopathy, venous occlusions, micro- and macroaneurysms, retinal ischemia and sickle cell retinopathy; (3) pediatric vascular disease including retinopathy of prematurify, Coat's disease, congenital vascular anomalies and choroidal neovascular membranes; (4) peripheral tumors including retinal and choroidal hemangiomas, choroidal melanomas and metastatic choroidal lesions.

BRIEF DESCRIPTION OF THE DRAWINGS

The invention description below refers to the accompanying drawings, of which.

DETAILED DESCRIPTION

Figure 1:
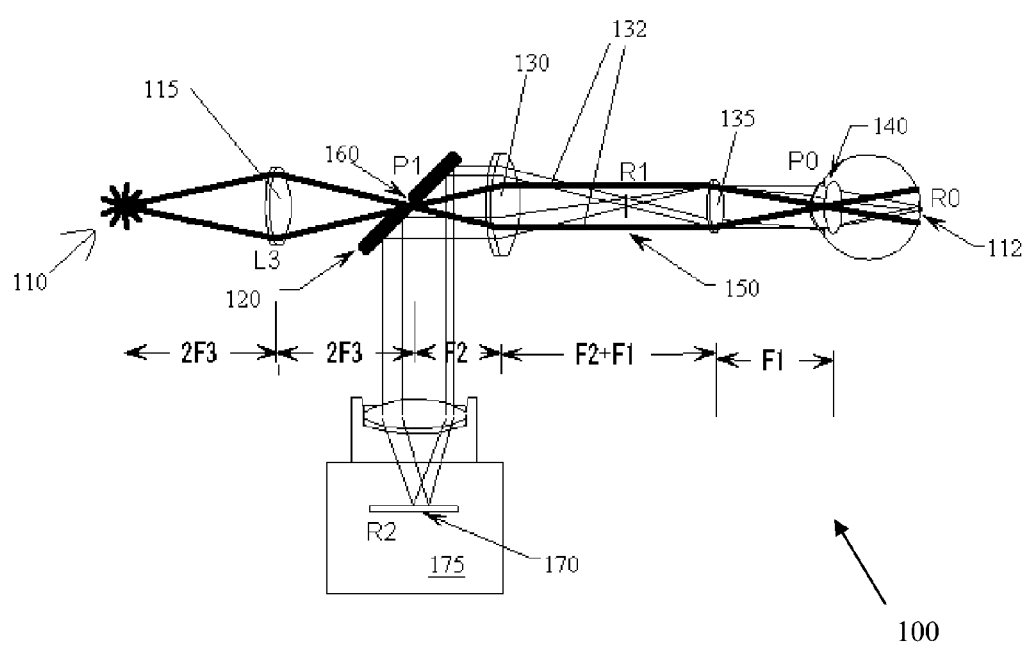
FIG. 1 is a schematic plan view of an infrared binocular indirect ophthalmoscope of the present invention.
Figure 2:
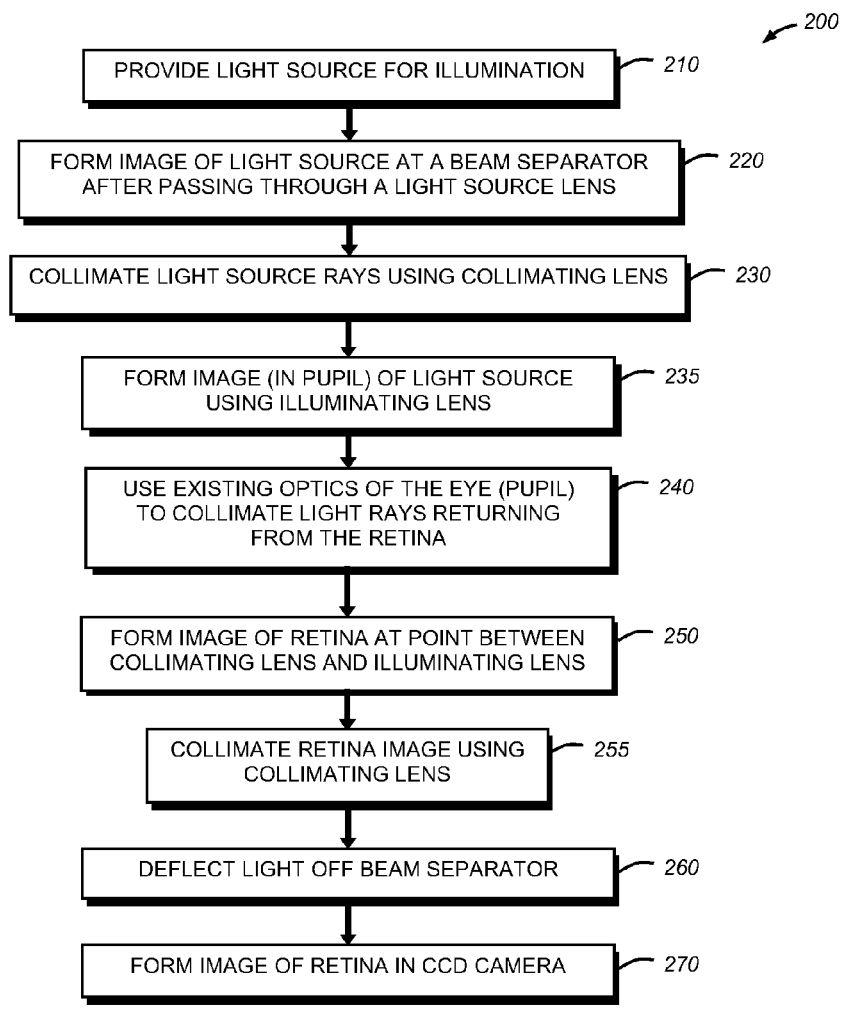
FIG. 2 is a block diagram detailing the general operating procedure for an infrared ophthalmoscope according to the illustrative embodiment.

FIG. 1 details a schematic plan view of the components of the infrared binocular indirect ophthalmoscope 100 of the present invention. FIG. 2 is a block diagram of a procedure 200 for operating the ophthalmoscope 100. The ophthalmoscope 100 differs from an original arrangement for the Schepens-type ophthalmoscope in that the imaging is performed in near-infrared as opposed to visible light. This compact instrument employs an LED device to illuminate the fundus in near-infrared, and collects the reflected light with solid state infrared detectors (of conventional design) using a specialized mounted stereo viewing screen (see image 170 of FIG. 1). Given that infrared light is invisible to the naked eye, an LED screen is provided for viewing of the reflected light. This image can readily be recorded in realtime, and transmitted over an appropriate communication link and/or network (a local area network, Internet, etc.) for telemedicine applications, where an ophthalmologist or other practitioner can examine images that are captured by an ordinary technician having minimal training Ocular examination with the opthalmoscope 100 does not generally require papillary dilatation, nor does it cause photophobia (ocular irritation from bright light). It can be used to perform rapid examination of the fundus for screening, and has wide application in examining patients in an environment where a fully dilated eye exam is not possible. This includes remote or medically underserved locations where a trained ophthalmologist is not available, but can be accessed remotely, as well as pediatric populations, emergency or disaster situations or trauma situations where examination of retina is necessary but pupillary response should be preserved for the examination.

As shown in FIG. 1 and operationally described in the procedure of FIG. 2, the infrared ophthalmoscope 100 includes a light source 110 provided at step 210. The light source 110 that comprises any device capable of transmitting light at the desired infrared or near-infrared frequencies discussed herein. The light source 110 can be a laser (diode-pumped, for example), LED, or other appropriate illuminating device.

The light is focused through a light source lens 115 located at twice its focal length ("2F3") from the light source 110, and is directed into a beam separator 120, also located at twice the focal length of the light source lens (2F3) from the light source lens 115. This forms an image of the light source at the beam separator, shown as operational procedure 200 of the infrared ophthalmoscope 100.

The light is then passed through a collimating lens 130 to collimate the light source rays (230 of FIG. 2). As shown, the light is collimated at 132 after passing through the collimating lens 130, and is located at its focal length (F2) from the beam separator 120. The light then passes through an illuminating lens 135 to form image in the pupil of the light source. The image is formed in the procedure 200 at step 235.

At operational procedure step 240 of FIG. 2, the existing optics of the eye collimates the light rays returning from the retina. As shown, the light passes through into the pupil 140 and is reflected through. The image of the retina is passed through the illuminating lens 135 and formed at the point 150 between the collimating lens and the illuminating lens. This is represented at 250 of the operational procedure 200.

The image of the retina is then collimated using the collimating lens 130, at step 255 of the operational procedure 200. This collimated light is then passed back to the beam separator 120 and at step 260, the majority of the image is deflected off the beam separator 120. The image is then deflected to display an image of the retina 170 as displayed or stored on the camera 175. The operational procedure 200 has the final element of forming the image of the retina in the camera at step 270.

Having now described the operational aspects of the infrared ophthalmoscope, its application to the examination and treatment of patients will now be described. The infrared ophthalmoscope can further include a photodynamic therapy light source. The treatment light source can be coupled to the ophthalmoscope via a fiber-optic cable. Further, the treatment beam can be delivered confocally with the infrared ophthalmoscope light source, such that an operator of the ophthalmoscope can simultaneously examine the area of the fundus which is to be treated, while also performing the PDT.

Figure 4:
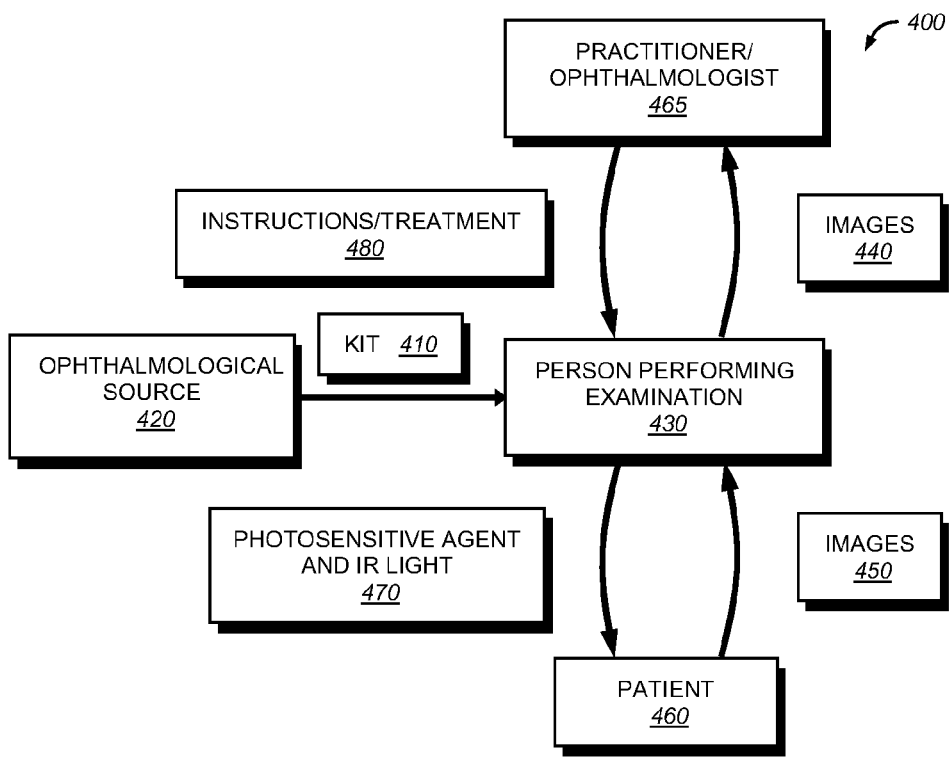
FIG. 4 is a block diagram showing a generalized interaction involving the employing of a kit for accomplishing the examination and treatment system and method according to the illustrative embodiment.

It is noted that, as shown in FIG. 1, the image of the retina is captured on a CCD camera 175. This allows a remotely located ophthalmologist or other practitioner to examine the images without the need to perform the procedure. Accordingly, a medic with basic training can employ the ophthalmoscope to obtain images of the retina. This flow of information and components of the system are described in greater detail with reference to FIG. 4, showing the parties to the procedure.

Figure 3:
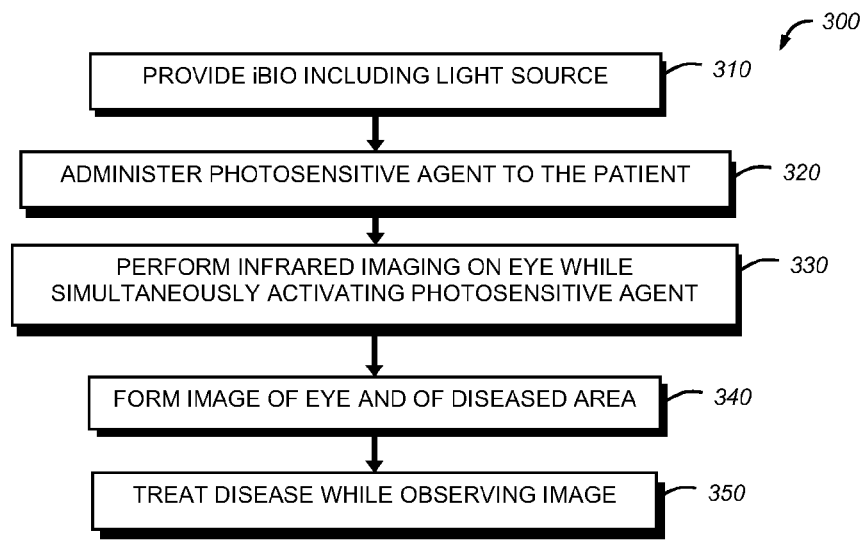
FIG. 3 is a block diagram detailing the combined treatment and examination procedure for an infrared ophthalmoscope according to the illustrative embodiment.

Reference is now made to FIG. 3, showing a treatment procedure employing an infrared ophthalmoscope and therapy light source according to the present invention. As shown by the treatment procedure 300, an infrared ophthalmoscope is provided at 310, including a therapy light source. The procedure 300 then administers a photosensitive agent to the patient at 320. The photosensitive agent can be any agent that is activated by a particular (predetermined) wavelength of light. For example, the wavelength of 869 nm allows for direct illumination of a lesion or other area of the eye, while also enabling safe agent activation in the retina. One exemplary agent is Verteporfin, a photosensitizing agent. The wavelength is a predetermined wavelengths selected to appropriately image and treat the eye of a human. A variety of other agents can be employed and the term "agent" as used herein should be taken broadly to include such photoreactive/photosensitive substances, which are safe for internal use by a patient.

The added treatment module allows for direct illumination of the lesion or other target portion of the eye being examined with a target beam and subsequent irradiation in the wavelength required for safe Verteporfin activation in the retina. More specifically, the wavelength of 869 nm is particularly effective at providing an image of the retina while simultaneously activating the Verteporfin. The lesion can be viewed in real time during the entire course of photodynamic therapy (PDT). There is provided a fiberoptic cable that connects the existing PDT laser devices to the treatment light source.

The imaging on the eye is then performed using the infrared ophthalmoscope to obtain an image of the retina while simultaneously activating the photosensitive agent at procedure step 330. An image of the eye, also showing the photosensitive agent for treatment purposes, is then formed at procedure step 340. The disease may then be treated at step 350 while the ophthalmologist or other assistance observes the original image.

The treatment procedure of FIG. 3 is for performing PDT on a plurality of eye diseases, including (1) choroidal neovascularization secondary to age-related macular degeneration and other inflammatory or idiopathic entities; (2) peripheral retinal vascular disease including diabetic retinopathy, venous occlusions, micro- and macroaneurysms, retinal ischemia and sickle cell retinopathy; (3) pediatric vascular disease include retinopathy of prematurity, Coat's disease, congenital vascular anomalies and choroidal neovascular membranes; (4) peripheral tumors including retinal and choroidal hemangiomas, choroidal melanomas and metastatic choroidal lesions. Macular PDT for combination therapy using Vertoporfin in combination with an anti-inflammatory treatment for wet age-related macular degeneration, and choroidal neovascularization (CNV) for other conditions including myopic and idiopathic CNV. Also, peripheral retinal PDT is especially useful for pediatric retinal conditions such as Coats disease, retinopathy of prematurity and retinoblastoma.

This methodology is particularly useful for treating peripheral lesions because the indirect ophthalmoscope provides a more facile view of the peripheral retina. It is relatively straightforward to simultaneously view large and more peripheral lesions and perform PDT on selected areas including the entire area. This is in contrast to slit-lamp technique which allows only for direct visualization of the posterior pole of the fundus using a contact lens. Peripheral viewing is more limited and it is more cumbersome to treat the peripheral retina with this system. The maximal limit for the size of infrared treatment beam (using the slit-lamp setup) is currently about 7.5 mm (in diameter). Larger lesions would require multiple sequential treatment protocols when the lesion is larger that 7.5 mm in diameter. Using the combination of indirect ophthalmoscopy with PDT, it would be easy to treat any size lesion, depending on the size of the condensor lens used (usually 20, 28 and 30 diopters of power. Given that an average eye has a diopteric power of 60 D, the 20D lens will give you 3× (60/20) magnification but a smaller field-of-view (approx 30-35%). The 30D lens will give you a 2× (60/30) magnification a larger field-of-view (approx. 40-45%).

Reference is now made to FIG. 4, showing a block diagram of a generalized interaction 400 employing a kit for accomplishing the examination and treatment apparatus and procedures discussed herein. Various components employed in the use of the examination and treatment of a human eye can be provided in an associated kit 410 as shown in the basic schematic diagram 400 of an exemplary treatment procedure according to the apparatus and method.

The kit 410 is provided by an ophthalmological source 420 or other appropriate entity to a person performing the examination 430. The person performing the examination 430 can transmit images 440 as received images 450 from a patient 460 to a practitioner 465. The person performing the examination 430 performs the procedure by providing photosensitive agent and infrared light 470 to the patient 460. If the practitioner 465 is located remotely from the person performing the examination 430, the images 440 are sent to the practitioner, and then instructions and/or treatment 480 can be issued to the person performing the examination 430. Alternatively, the person performing the examination 430 can be the practitioner or ophthalmologist 465, in which case they directly examine the patient 460 and issue treatment accordingly. The kit treatment of FIG. 4 is one exemplary practical application of the ophthalmoscope for performing examination and treatment of the human eye.

It should be clear that the system and method of the invention can be used advantageously to overcome a variety of problems and disadvantages present in prior ophthalmoscopes. For example, the human eye does not see infrared light and there is no papillary response. The exam is comfortable and without light sensitivity. Particularly, in a pediatric eye practice, this ensures better patient compliance with the exam or treatment. This further allows a physician to perform a greater number of examination within limited clinical hours without using dilating eye drops and avoiding the potential for allergic reaction or irritation from the drops.

Also, in a service branch (i.e. local, state or federal government service) an examiner can rapidly determine the presence or severity of an injury. This is particularly useful in the field where service branch members can return to duty immediately without dilated pupils and resulting temporary vision deficit if no injury is found. This exam can be performed by a medic with minimal training, as discussed herein. Additionally, in subjects who have received traumatic brain injury, head injury, or are unresponsive and require neurological monitoring (which usually includes examination of the papillary response), the fundus can be examined without the need for papillary dilatation.

Furthermore, longer wavelengths of light (red-infrared) evoke deeper penetration of retinal tissue to provide superior images and allow better visualization of deep retinal and choroidal layers than standard visible (white) light ophthalmoscopes. This is important in screening for choroidal diseases and injuries including macular pathologies such as AMD (age-related macular degeneration, TBI, laser-induced macular burns, choroidal hemorrhage and rupture, and tumors. The combined examination and treatment procedures described herein can be used to treat a large number of diseases and injuries including choroidal neovascularization secondary to age-related macular degeneration and other inflammatory or idiopathic entities; peripheral retinal vascular disease including diabetic retinopathy, venous occlusions, microaneurysms and macroaneurysms, retinal ischemia and sickle cell retinopathy; pediatric vascular disease include retinopathy of prematurity, Coat's disease, congenital vascular anomalies and choroidal neovascular membranes; peripheral tumors including retinal and choroidal hemangiomas, choroidal melanomas and metastatic choroidal lesions.

The following describes the potential for combining other imaging modalities known to those of skill in the art with the infrared binocular indirect ophthalmoscope of the illustrative embodiment.

The infrared binocular indirect ophthalmoscope (iBIO) can be combined with the following imaging modalities, among others, to perform simultaneous imaging and anatomical and physiological scanning. For example, the iBIO can be combined with an optical coherent tomography (OCT), which uses infrared wavelengths for scanning OCT can compute retinal thickness maps and provide cross-sectional retinal anatomical images. These two modalities can be combined to obtain OCT information over the area imaged by the iBIO. Then, OCT scans can be digitally projects over the retinal area observed by the iBIO examiner.

Also, the iBIO imaging can be combined with laser Doppler measurements of retinal blood flow. Laser Doppler imaging is usually performed in the infrared range. It is possible to measure the speed of blood flow in selected retinal vessels at time of the iBIO examination.

The iBIO imaging can further be combined with focal electroretinogram (ERG) of the macula or retinal periphery. During iBIO examination, the macula can be stimulated with which, red and blue "flash" light to simulate photopic and scotopic ERG testing and the electric response of photoreceptors can be measured over the macular area or selected retinal periphery. This provides physiological information on the function of photoreceptors in the area of interest.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the ophthalmoscope can be used to examine patients with a wide range of retinal diseases including diabetic retinopathy, age-related macular degeneration, retinal vascular disease, other macular conditions, traumatic injuries including laser exposure burns, ocular tumors, retinal degenerations and pediatric ocular conditions. In the PDT treatment employing the ophthalmoscope of the present invention, it can be used to treat wet age-related macular degeneration, choroidal neovascularization and peripheral vascular lesion, and tumors. Accordingly, this description is meant to be taken only by way of example, and not to otherwise limit the scope of this invention.

What is claimed is:

1. An infrared binocular indirect ophthalmoscope for imaging and treatment on a human eye, the infrared binocular indirect ophthalmoscope comprising:
   an infrared light source that generates infrared light;
   a beam separator defining a hole, the infrared light forming a first image of the light source at the beam separator;
   a collimating lens that collimates the infrared light, the collimating lens having a first focal length and being separated from the beam separator the first focal length;
   an illuminating lens that focuses the infrared light to form a second image of the light source in a pupil of the human, the illuminating lens having a second focal length and being separated from the collimating lens by a distance equal to a sum of the first focal length and second focal length; and
   a treatment beam confocally transmitting with the infrared light and passing through the hole defined by the beam separator, such that the treatment beam is coaxial with the infrared light source and passes through to the human eye to activate a photosensitizing agent that performs treatment on a treatment area of the human eye, the treatment beam causing activation of the photosensitizing agent when operating at a predetermined wavelength,
   wherein the second image is reflected and passes through the illuminating lens and collimating lens such that it is deflected onto a camera to form a third image of a retina of the human eye, the third image of the retina representing a field of view, wherein the treatment area includes an entirety of the field of view
   wherein an optical power of the illuminating lens is at least one of a first optical power and a second optical power greater than the first optical power, wherein the first optical power produces a first magnification of the field of view and a first size of the field of view and the second optical power produces a second magnification of the field of view and a second size of the field of view, such that the first magnification is greater than the second magnification and the second size of the field of view is greater than the first size of the field of view.

2. The system of claim 1 wherein the predetermined wavelength is 869 nm.

3. The system of claim 1 wherein the infrared light source is a light emitting diode and the treatment beam is also a light emitting diode.

4. The system of claim 1 wherein the photosensitizing agent is Verteporfin.

5. A method for using an infrared binocular indirect ophthalmoscope for imaging and photodynamic therapy, the method comprising:
   providing an infrared binocular indirect ophthalmoscope including a light source for illumination, the ophthalmoscope including a first illuminating lens having a first optical power;
   providing a treatment beam confocally and coaxially with the light source for performing the photodynamic therapy, the treatment beam operating at a predetermined wavelength that causes activation of a photosensitizing agent injected into a person; and
   generating an image of a field of view of the retina while simultaneously providing treatment to a treatment area of a human eye using the infrared binocular indirect ophthalmoscope with the treatment beam, treatment area including an entirety of the field of view;
   replacing the first illuminating lens with a second illuminating lens having a second optical power, the second optical power being greater than the first optical power such that the second illuminating lens provides an increased field of view and a decreased magnification.

6. The method of claim 5 further comprising transmitting the image of the retina to an ophthalmologist for examination, wherein the ophthalmologist is located remotely from the infrared binocular indirect ophthalmoscope.

7. A kit for imaging and treatment of a human eye for carrying out the method of claim 5.

8. The system of claim 1, wherein a first diameter of the field of view is equal to a second diameter of the treatment area.

9. The system of claim 1, wherein the treatment area is 7.5 mm in diameter.

10. The method of claim 5, wherein a first diameter of the field of view is equal to a second diameter of the treatment area.

11. The method of claim 5, wherein the treatment area is 7.5 mm in diameter.

* * * * *